United States Patent [19]

Ichihara

[11] Patent Number: 4,864,500
[45] Date of Patent: Sep. 5, 1989

[54] IMAGE PROCESSING FOR PHOTOGRAPHING SCINTIGRAM OF SUBJECT ON X-RAY FILM AT OPTIMUM DENSITY

[75] Inventor: Takashi Ichihara, Ootawara, Japan

[73] Assignee: Kabushiki Kaisha Toshiba, Kawasaki, Japan

[21] Appl. No.: 848,036

[22] Filed: Apr. 4, 1986

[30] Foreign Application Priority Data

Apr. 5, 1985 [JP] Japan .................................. 60-72011

[51] Int. Cl.$^4$ ........................ H04N 5/14; G06F 15/42
[52] U.S. Cl. .......................... 364/413.24; 364/413.13; 250/363.02
[58] Field of Search ........................ 364/414; 378/901; 250/363, 363 S, 369

[56] References Cited

U.S. PATENT DOCUMENTS

| | | | |
|---|---|---|---|
| 4,323,977 | 4/1982 | Arseneau | 364/571 |
| 4,346,409 | 8/1982 | Ishida et al. | 364/414 |
| 4,386,404 | 5/1983 | Knoll et al. | 364/414 |
| 4,438,495 | 3/1984 | Collins et al. | 364/414 |
| 4,454,606 | 6/1984 | Relihan | 364/414 |
| 4,529,883 | 7/1985 | Yamakawa et al. | 250/363 S |
| 4,611,283 | 9/1986 | Lumelsky et al. | 250/369 |

OTHER PUBLICATIONS

English translation & original German of German Patent Office, Office Action in German Ser. No. P 35 38 845.5-33, dated Jan. 29, 1987.

Knopp et al., "Kerntechnik", vol. 16, 1974, No. 8/9, pp. 372 to 379.

Primary Examiner—Charles E. Atkinson
Assistant Examiner—Kimthanh T. Bui
Attorney, Agent, or Firm—Finnegan, Henderson, Farabow, Garrett & Dunner

[57] ABSTRACT

A diagnostic nuclear medical apparatus comprises a digital scintillation camera unit for detecting radiation from a subject to provide a radiation count signal, a data processing unit for converting the count signal from the camera unit into video information and a video imager for receiving the video information and photographing the scintigram of the subject on an X-ray film. In the video imager, a test pattern is photographed on an X-ray film. A video to photographic density conversion characteristic of the developed X-ray film is measured, and the measured data is loaded into the data processing unit. The average value and standard deviation value of the radiation detection counts per pixel of a region-of-interest of the subject are computed, and the display upper count level is computed according to these values. A count to gray conversion table such that the upper count level corresponds to the maximum photographic density on the film and the conversion of the count to photographic density on the film becomes linear, is obtained according to the measured data and the upper count level. The count signals from the camera unit are converted according to a conversion table into video signals having gray levels to be supplied to the video imager.

5 Claims, 6 Drawing Sheets

IMAGE PROCESSING FOR PHOTOGRAPHING SCINTIGRAM OF SUBJECT ON X-RAY FILM AT OPTIMUM DENSITY

BACKGROUND OF THE INVENTION

This invention relates to a diagnostic nuclear medical apparatus and, more particularly, to image processing for an apparatus using a digital scintillation camera.

Diagnostic nuclear medical apparatuses are utilized for the diagnosis of subjects (human patients) through detection of the distribution of gamma rays emitted from the subject dosed with radioisotopes (hereinafter referred to as RI). In a prior art gamma camera system, gamma rays emitted from the interior of the subject are detected by a gamma camera having a two-dimensional detection surface, and position signals indicative of positions at which gamma rays are detected are fed to a gamma imager. The gamma imager exposes an X-ray film with luminescent spots according to the detected distribution of the gamma rays to obtain a scintigram (an RI distribution image).

Recently, digital scintillation camera systems have been applied in practice to obtain a scintigram of subject. Diagnostic data (position data) obtained from a scintillation camera is converted by an analog-to-digital converter into digital data for storage in an image memory. In the memory, the number of times (i.e., counts) gamma rays are detected at each position (i.e., each pixel on the detection surface of the camera) is stored as data. Data is read out from the image memory in the order of addresses corresponding to picture elements on the camera detection surface for conversion by a digital-to-analog converter into analog information. The analog information is further converted into a video signal for displaying the RI detection times at graduated levels of brightness. The video signal is fed to a video imager to display a luminescent spot image on a TV monitor. The luminescent spot image is imaged (photographed) by a multi-format camera on an X-ray film. A portion of the subject where the RI detection count is large is displayed with high brightness on the TV monitor. A portion where the RI detection count is high, on the other hand, is imaged black on the X-ray film, i.e., it is photographed at a high photographic density. The relation between the video signal amplitude level and X-ray film photographic density is peculiar to a film photographing system (including a TV monitor, X-ray film, developing unit and liquid developer).

With such a diagnostic apparatus, in many cases, a contrast between a region-of-interest and other regions imaged on the X-ray film provides important information for the diagnosis. Therefore, it is desired to photograph the region-of-interest at an optimum density. Otherwise, erroneous diagnosis is liable to result.

In the digital scintillation camera system, the video signal gray scale (GRAY) has 256 levels from 0 to 255, for instance. The display count scale (WINDOW), i.e., the gamma ray detection times, has 4,096 count levels of 0 to 4095, for instance. The display gray scale level is linearly proportional to the video signal amplitude level (in volts). The GRAY scale and WINDOW scale may be arbitrarily set through a keyboard of a computer system by an operator. For example, 10 to 50 counts may be made to correspond to a gray scale of 20 to 100. For this reason, it is possible to freely determine the relation between the WINDOW level and X-ray film photographic density. Once this relation is determined, the relation the WINDOW level and GRAY scale can be determined.

The quality such as density and contrast of image on the X-ray film is influenced by the type of an X-ray film used, an elapsed period after the manufacture of the film, and developing conditions (developing unit, liquid developer, etc.). The upper and lower limits of gamma-ray detection counts depend on the kind of an organ to be diagnosed and the kind of a radioactive medicine used. Therefore, the image quality is also influenced by these conditions. Therefore, in order to obtain the optimum image quality for the diagnosis, it is necessary to determine optimum image processing conditions for each diagnosis. This is, however, time-consuming.

A copending U.S. patent application No. 793,767 entitled "Digital Scintillation Camera System" filed on Nov. 1, 1985 and assigned to the same assignee as this application discloses an improved digital scintillation camera system.

SUMMARY OF THE INVENTION

An object of the invention is to provide an improved digital scintillation camera system.

Another object of the invention is to provide a digital scintillation camera system which enables all subjects of diagnosis to be photographed on an X-ray film at an optimum image quality for diagnosis on condition that the characteristics of a film photographing system remain constant.

A diagnostic nulcear medical apparatus of this invention comprises a digital scintillation camera unit including a two-dimensional radiation detector and for detecting radiations from the inside of a subject dosed with radioisotope for each of pixels arranged in a two-dimensional array to provide detection data representing the counts of detection of radiations in the form of a digital signal; data processing means coupled to the digital scintillation camera unit for converting radiation detection digital data into analog video information; and video imaging means coupled to the data processing means for visually displaying a scintigram image representing the radioisotope distribution of the subject, the scintillation image displayed by the video imaging means being photographed on a photographic film, and the photographic density of the film resulting from a developing process being a function of the amplitude level of the analog video information.

According to the invention, to achieve the above objects, the data processing means is arranged to convert the digital data into the analog information such that the conversion characteristic of the radiation detection level to the photographic density of a scintigram image on the developed film is made substantially linear.

DETAILED DESCRIPTION OF THE PREFERRED EMBODIMENT

Figure 1:
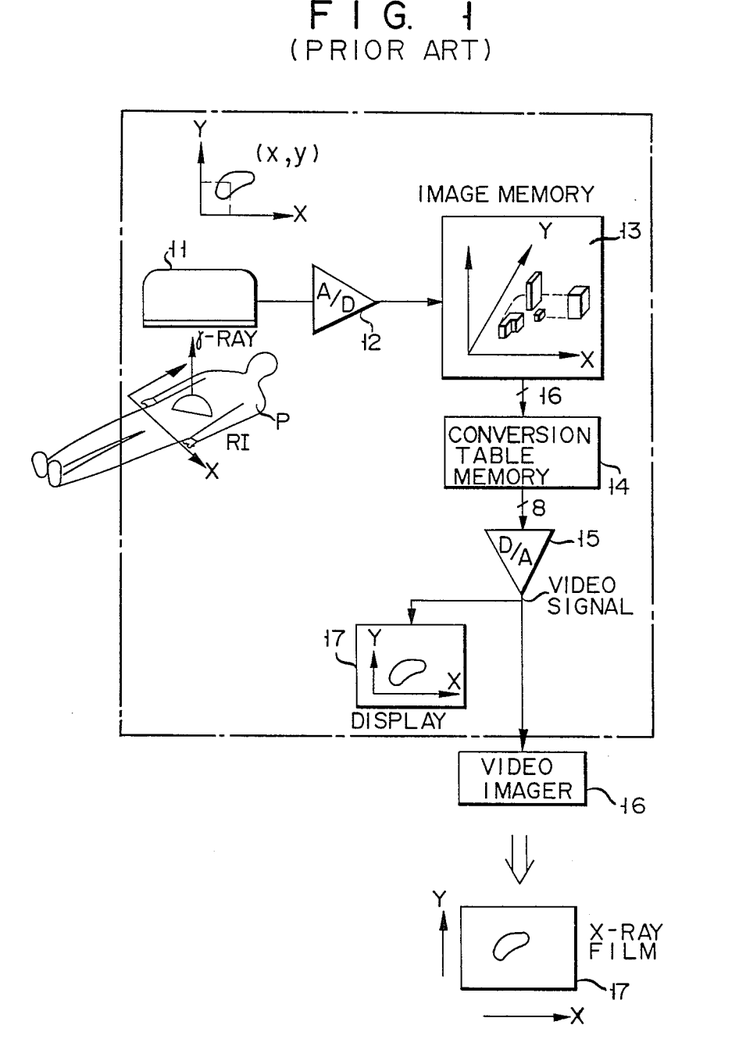
FIG. 1 shows a prior art digital scintillation camera system.

For better understanding of the invention, a prior art digital scintillation camera system will now be described with reference to FIG. 1.

Gamma rays emitted form the inside of subject P with RI dosed are detected by scintillation camera (gamma camera) 11. Camera 11 progressively provides analog position data with a magnitude corresponding to a gamma ray detection count for each pixel on a detection surface having X-Y co-ordinates, according to the sequence of arrangement of pixels. A/D converter 12 converts analog position data into 16-bit digital data. Digital data corresponding to pixels on the detection surface are successively stored in locations of image memory 13 in a data processing section which correspond to the positions of the pixels. 16-bit digital data is progressively read out from image memory 13 to be applied to conversion table memory 14. Conversion table memory 14 converts 16-bit digital data into 8-bit digital data. This means a provision of a display gray scale having 256 ($=2^8$) gradations from 0 to 255. D/A converter 15 converts 8-bit digital data into analog data. D/A converter 15 converts digital data of the highest gray level of 255 to analog data of the maximum amplitude level of, for instance, 0.7 volts. Analog data of 0 to 0.7 volts is applied to video imager 16 to display a scintigram in 256 gradations on a TV monitor. A bright spot image on the TV monitor is photographed by a multi-format camera onto X-ray film 17. Analog data is also applied to data processing display 17. A region-of-interest is set while watching an image on display 17.

Figure 2:
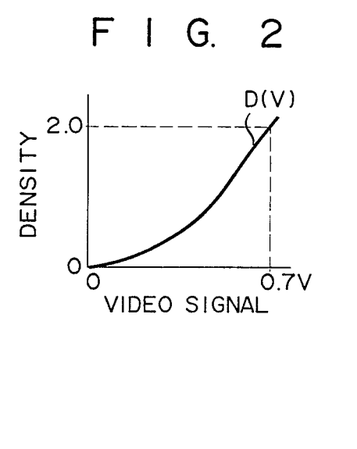
FIG. 2 is a graph showing a conversion characteristic of video signal to a photographic density, which is peculiar to a film photographing system.

FIG. 2 shows a characteristic of video imager 16, i.e., a characteristic of conversion of video signal level to X-ray film photographic density. The video signal maximum level of 0.7 volt is converted into the maximum photographic density level of 2.0. The shape of conversion characteristic curve shown in FIG. 2 varies with the type of X-ray film used and development conditions.

Figure 3:
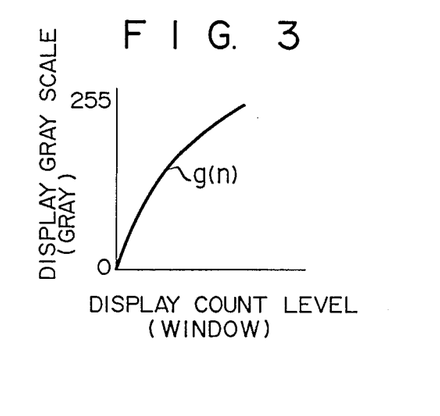
FIG. 3 is a graph showing a window scale-to-gray scale convertion characteristic which can be freely set.

FIG. 3 shows a characteristic of conversion of WINDOW level to GRAY level. This characteristic is set in conversion table memory 14 of FIG. 1. This conversion characteristic can be desirably set by rewriting the content in conversion table memory 14. The conversion characteristic is determined by a characteristic of conversion of WINDOW level to photographic density that the operator desires.

Figure 4:
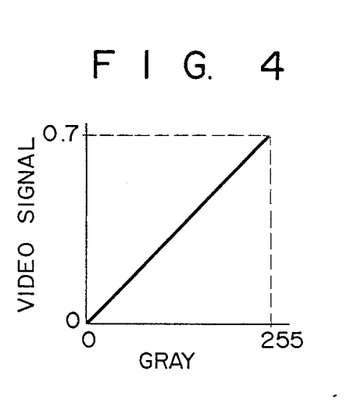
FIG. 4 is a gray scale-to-video signal conversion characteristic.

FIG. 4 shows a GRAY scale to video signal level conversion characteristic of D/A converter 15. It will be seen that the video signal level is linearly proportional to the GRAY scale.

Figure 5:
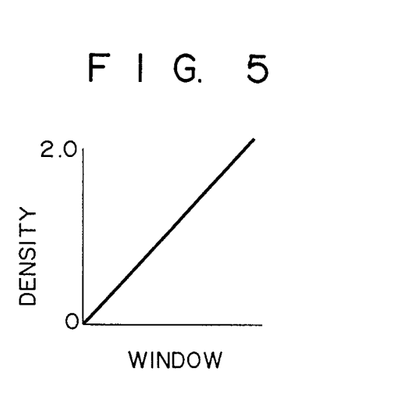
FIG. 5 is the optimum window scale-to-density conversion characteristic.

The characteristic of FIG. 2 shows that the maximum count of 4,095 is converted to the maximum photographic density of 2.0. The maximum count varies depending on the kind of organs to be diagnosed and the kind of radioactive medicine used. Therefore, when the maximum count is considerably smaller than 4,095, it is impossible to obtain a scintigram with a contrast suited for diagnosis. The invention intends to obtain an X-ray image with an optimum contrast for diagnosis irrespective of the maximum gamma ray detection count. Accordingly, a feature of the invention resides in automatically setting in a conversion table memory the WINDOW level to gray scale conversion characteristic shown in FIG. 3, which enables WINDOW level to photographic density characteristic as shown in FIG. 5 to be linear, with the aid of detection data from the scintillation camera, and a video signal level to photographic density conversion characteristic shown in FIG. 2 which can be known from a measurement.

Now, the image processing in accordance with the invention will be described. The processing according to the invention comprises two stages, i.e., a preprocessing stage of measuring the characteristic of the film photographing system and a image collection stage for diagnosis.

Figure 6:
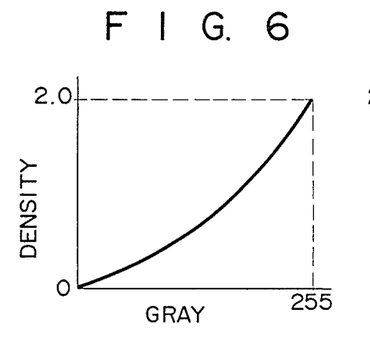
FIGS. 6 to 8 are graphs for explaining image processing according to the invention.

In the pre-processing stage, a 16-gradation test pattern video signal, which indicates a test pattern having 16 gradations obtained by dividing the gray scale of 0 to 225 levels an equal step size, is fed to the video imager to be displayed on a TV monitor. The test pattern image on the TV monitor is photographed by a multi-format camera to obtain an X-ray film image for testing. This X-ray film image has a gray level to photographic density conversion characteristic D (G) as shown in FIG. 6. This conversion characteristic is peculiar to a film photographing system. The X-ray film image is measured by a film density meter so that the density level is read for each of 16 gradations of the test pattern. The measurement data of the X-ray film image is fed through a keyboard to a computer, in which the gray level to photographic density conversion characteristic is filed in a memory in the form of a data table.

In the actual image collection stage, a region-of-interest is set on a data collection display where a diagnostic image is displayed. The gamma ray detection count for each picture element in the region-of-interest is checked, and an average AV per one pixel of the counts is computed. Further, a standard deviation value SD of counts per one pixel of the region-of-interest is computed. From the average value AV and standard deviation value SD, display window upper level WU is computed as follows:

$$WU = AV + a \times SD \tag{1}$$

where a is an experimentally determined constant and, for instance, 3.

Figure 7:
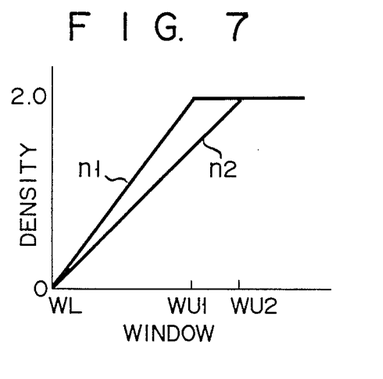

In this embodiment, upper and lower levels WU and WL of the display window are made to correspond to the maximum and minimum density levels 2.0 and 0 of the photographic density, respectively, as shown in FIG. 7. A data table showing a WINDOW level to photographic density conversion characteristic which changes linearly between WL and WU is prepared by the computer and stored as data table in a memory. In FIG. 7, conversion characteristics n1 and n2 corresponding to display window upper levels WU1 and WU2 in different examples of diagnosis are shown.

Figure 8:
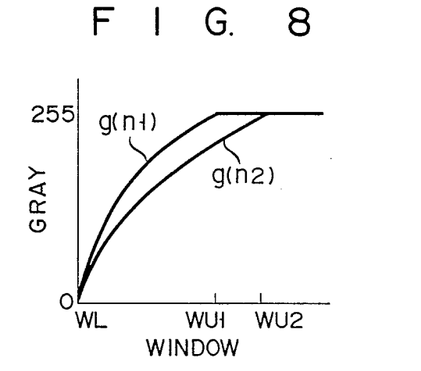

The computer refers to the data tables showing the characteristics of FIGS. 6 and 7 to prepare a data table of a window level to gray scale conversion characteristic shown in FIG. 8. This data table is prepared by reading out the window level and the gray level corresponding to a photographic density level. FIG. 8 shows conversion characteristics g(n1) and g(n2) corresponding to window upper levels WU1 and WU2. The conversion characteristic of FIG. 8 corresponds to an inverse function $D^{-1}(G)$ of the conversion characteristic $D(G)$ of FIG. 6.

The window level to gray level conversion table thus obtained is loaded into a conversion table memory. As a result, the diagnostic image data read out from the image memory is converted into a gradation image data according to the characteristic shown in FIG. 8. With this image data fed to the video imager, an X-ray image is obtained which has a characteristic in which the density level is linearly proportional to the window level as shown in FIG. 7. Therefore, it will be understood that all the diagnostic X-ray images are obtained at an optimum image quality irrespective of the upper counts of the gamma ray detection unless the characteristic of the film photographing system shown in FIG. 6 is changed.

Figure 9:
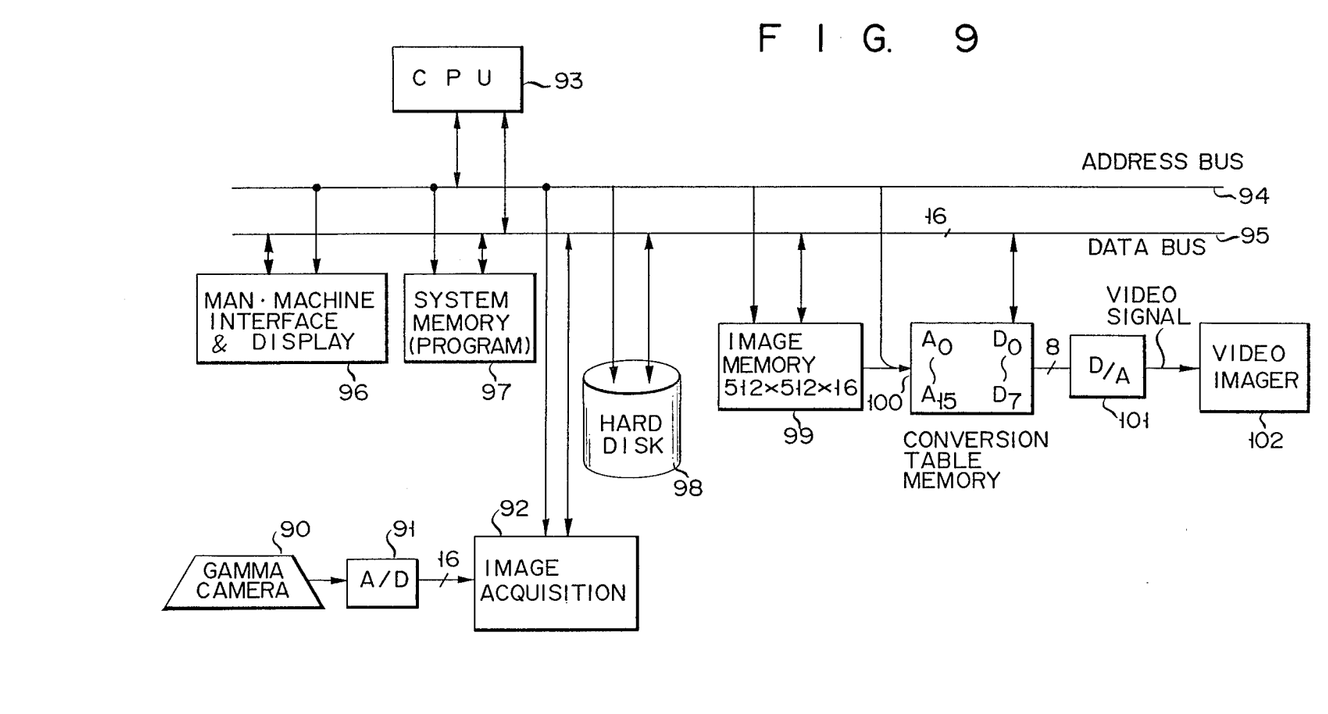
FIG. 9 shows a schematic arrangement of a digital scintillation camera system according to the invention.

Now, the arrangement of the digital scintillation camera system according to the invention will be described with reference to FIG. 9. Gamma ray measurement data detected by gamma camera 90 is converted by A/D converter 91 into 16-bit digital image data for each pixel. The digital image data is coupled to image data collection section 92. Image collection section 92 is coupled to central processor unit (CPU) 93 through address bus 94 and data bus 95. Man-machine interface 96, system memory 97 storing operation programs, hard disk unit 98, image memory 99 and conversion table memory 100 are also coupled to CPU 93 via address bus 94 and data bus 95. Conversion table memory 100 is coupled to video imager 102 through D/A converter 101. Image memory 99, conversion table memory 100 and D/A converter 101 constitute a count to video signal conversion section.

Figure 10:
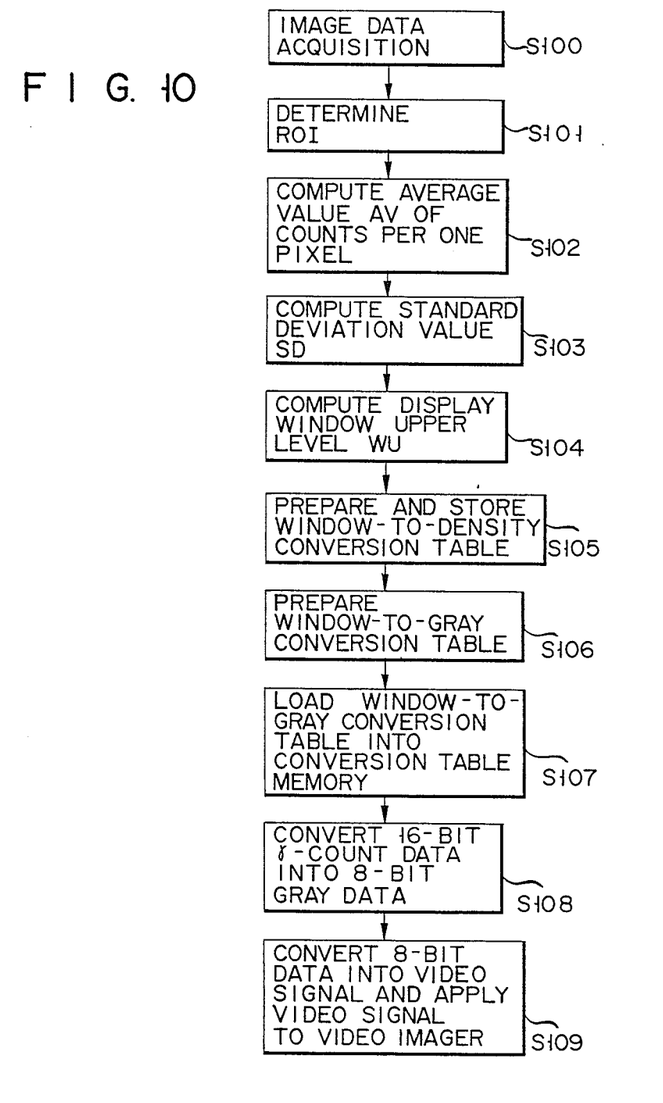
FIG. 10 is a flow chart for explaining image processing according to the invention.

Image data collected in image data collection section 92 is stored in hard disk unit 98. Data table showing the characteristic of the film photographing system shown in FIG. 6, obtained in the pre-processing stage described before, is in advance stored in hard disk unit 98 through man-machine interface 96. To photograph a diagnostic image, image data is transferred from hard disk unit 98 to image memory 99. Image memory 99 has a capacity of storing 16-bit data for each of 512×512 pixels, for instance. This operation corresponds to an image collection step S100 shown in FIG. 10.

Man-machine interface 96 includes data collection display, on which a diagnostic image is displayed. By watching the diagnostic image a region-of-interest (ROI) having a size of 3×3 cm², for instance, in the diagnostic image is set using track ball and numeral keys (step S101). CPU 93 reads in image data of the region-of-interest from hard disk unit 98 or image memory 99. CPU 93 checks the counts for each pixel in the region-of-interest and computes the average value AV of counts per pixel (step S102). Subsequently, CPU 93 computes standard deviation value SD (step S103). CPU 93 further computes display window upper level WU from average value AV and standard deviation value SD according to equation (1) (step S104). CPU 93 prepares a data table representing a line connecting a point (WU, 2.0 of photographic density) and a point (WL=0, 0) as shown in FIG. 7 and stores it in hard disk unit 98 (step S105). CPU 93 prepares the conversion table as shown in FIG. 8 by referring to the data table shown in FIG. 6 and data table shown in FIG. 7 stored in hard disk unit 98 (step S106). CPU 93 loads the conversion table into conversion table memory 100. 16-bit image data is read out from image memory 99 to be converted by conversion table memory 100 into 8-bit image data (step S108). Conversion table memory 100 is addressed by 16-bit data to provide 8-bit data. 8-bit data from the conversion table memory is converted by D/A converter 101 into analog data which is applied to video imager 102 to obtain a scintigram (step S109).

Figure 11:
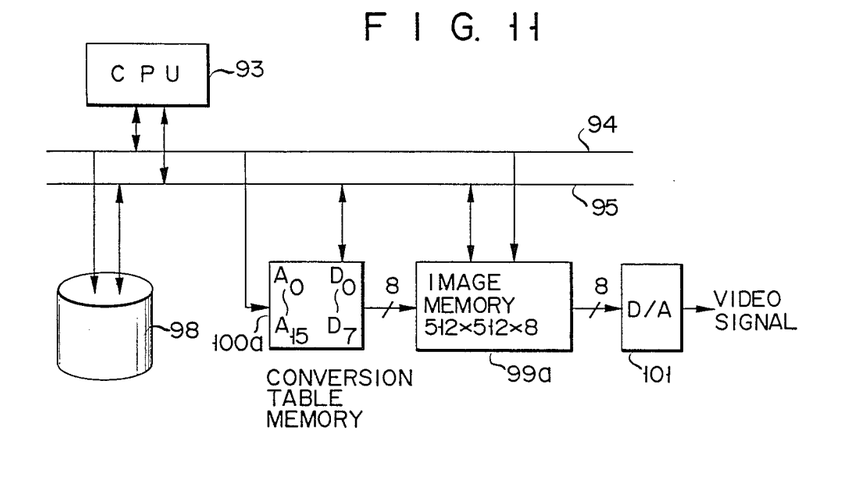
FIG. 11 shows a modification of the arrangement shown in FIG. 9.

FIG. 11 shows a modification of the count to video signal conversion section. In this example, conversion table memory 100a is disposed ahead of image memory 99a. Conversion table memory 100a has 16 bit address inputs and 8 bit data outputs. Image memory 99a has a capacity of 512×512×8 bits. 8-bit conversion data from CPU 93 is written into conversion table memory 100a. To write the data, 16-bit image data read out from hard disk unit 98 in the order of pixels is transferred through a bus controller (not shown) from data bus 95 to address bus 94 to thereby access conversion table memory 100a. Image memory 99a is accessed in the order of pixels for writing 8-bit data from conversion table memory 100a. In this embodiment, the capacity of image memory 99a may be less than that of the image memory shown in FIG. 9.

Figure 12:
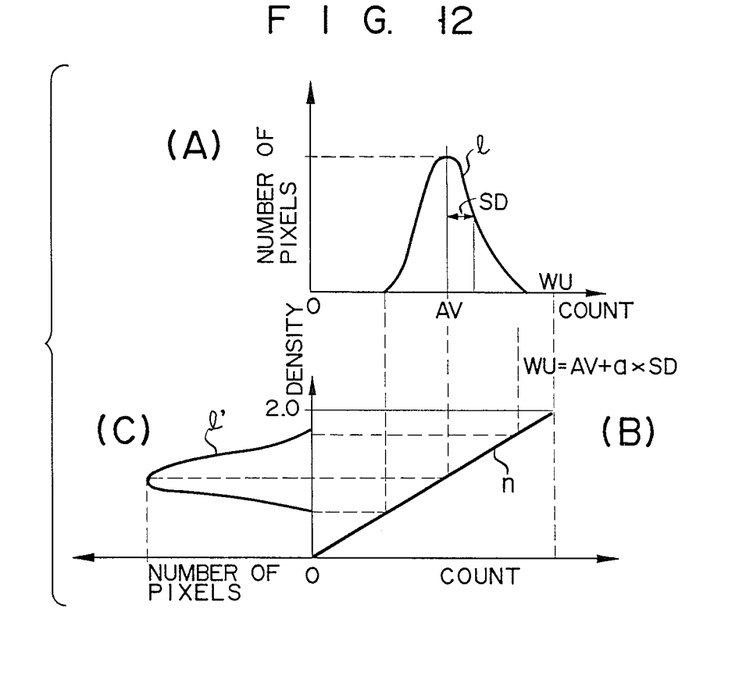
FIG. 12 is a graph for explaining the image processing according to the invention.

FIG. 12 is a graphical representation of the image processing according to the invention so far described. FIG. 12(A) is a graph showing a RI distribution in ROI. In the Figure, the ordinate is taken for the number of pixels, and the abscissa is taken for count. The display window upper level WU is computed from the average count AV per pixel and standard deviation SD according to equation (1). As shown in FIG. 12B, a linear count to photographic density conversion characteristic is obtained, in which WU corresponds to a photographic density of 2.0. With this conversion characteristic, the distribution 1 of numbers of pixels with respect to counts, is converted into a distribution 1 of numbers of pixels with respect to photographic density according to which a ROI scintigram image has an optimum density on an X-ray film, as shown in FIG. 12(C). That is, the characteristic of the film photographing system is corrected so that the ROI is photographed on the X-ray film with the best quality suited for diagnosis.

The ROI may be a lattice ROI, which divides the display into a plurality of units, for instance 32×32 units. In this case, the count average is obtained for each ROI, and the display window upper level WU is computed for the ROI having the maximum average value of count.

What is claimed is:

1. A diagnostic nuclear medical apparatus comprising:
    a digital scintillation camera unit including a two-dimensional radiation detector for detecting radiation from the inside of a subject with radioisotope dosed for each of pixels arranged in a two-dimensional array to provide detection data, representing counts of detection of radiation, in the form of a digital signal;
    data processing means coupled to said digital scintillation camera unit for converting the radiation detection digital signal into an analog video information signal; and
    video imaging means coupled to data processing means for visually displaying a scintigram image representing the radioisotope distribution of said subject, the scintigram image displayed by said video imaging means being photographed on a photographic film, and the photographic density of the film after a developing process being a function of the amplitude of the analog video information signal;

said data processing means being arranged to convert the digital signal into the analog information signal such that a substantially linear characteristic of conversion of radiation detection level to photographic density is obtained on a developed film.

2. A diagnostic nuclear medical apparatus comprising:

a digital scintillation camera unit including a two-dimensional radiation detector for detecting radiation from the inside of a subject with radioisotope dosed for each of pixels arranged in a two-dimensional array to provide detection data, representing counts of detection of radiation, in the form of a digital signal;

data processing means coupled to said digital scintillation camera unit for converting the radiation detection digital signal into an analog video information signal; and video imaging means coupled to data processing means for visually displaying a scintigram image representing the radioisotope distribution of said subject, the scintigram image displayed by said video imaging means being photographed on an X-ray film, said video imaging means including a means for measuring in advance and loading as a first conversion table into said data processing means the photographic density of the film after a developing process as a function of the amplitude level of the analog video information signal, and said developed film image having a maximum photographic density and a minimum photographic density;

said data processing means being arranged to obtain, from detection data of a region-of-interest of the subject, an average value of radiation detection level per one pixel and a standard deviation value of radiation detection level, compute an upper detection level to be displayed as said maximum photographic density on the film from the average value and standard deviation value, prepare a second conversion table such that said photographic density varies linearly from a lower detection level corresponding to said minimum photographic density up to the upper detection level, prepare from said first and second conversion tables a third conversion table for converting the radiation detection level to the amplitude level of analog video information signal so that the density of the scintigram of the subject on the x-ray film varies linearly from the lower detection level to the upper detection level, and correct the detection data from said digital scintillation camera unit according to said third conversion table.

3. The diagnostic nuclear medical apparatus according to claim 2, wherein said data processing means includes:

an image memory for storing the detection data from said digital scintillation camera unit;

a conversion table memory for storing said third conversion table, said conversion table memory being accessed by a signal corresponding to said detection data reach out from said image memory; and digital-to-analog conversion means for converting output data read out from said conversion table memory into an analog information signal to be applied to said video imaging means.

4. The diagnostic nuclear medical apparatus according to claim 2, wherein said data processing means includes:

a conversion table memory for storing said third conversion table, said conversion table memory being accessed by a signal corresponding to said detection data from said scintillation camera unit;

an image memory accessed by an address signal corresponding to said detection data from said scintillation camera unit to store output data read out from said conversion table memory; and digital-to-analog conversion means for converting data read out from said image memory into an analog information signal to be applied to said video imaging means.

5. A method of photographing a scintillation image of a subject on a film at a density best suited for diagnosis and for use in a diagnostic nuclear medical apparatus, said developed film image having a maximum photographic density, comprising a digital scintillation camera unit including a two-dimensional radiation detector for detecting radiation dosed for each of pixels arranged in a two-dimensional array to provide detection data, representing counts of detection of radiation, in the form of a digital signal; data processing means coupled to said digital scintillation camera unit for converting the radiation detection digital data into an analog video information signal; and video imaging means coupled to data processing means for visually displaying a scintigram image representing the radioisotope distribution of said subject, the scintigram image displayed by said video imaging means being photographed on a photographic film;

said method comprising the steps of:

measuring a characteristic of conversion of a video signal to photographic density on a developed film by supplying a test pattern video signal to said video imaging means;

preparing a first conversion table showing the measured characteristic of conversion of video signal to photographic density in said data processing means;

displaying a scintigram image of the subject by counting radiation emitted from the subject in said video imaging means;

setting a region-of-interest in the scintigram image of the subject;

computing an average value AV and standard deviation value SD of the radiation detection count per pixel in the region-of-interest in said data processing means;

computing in said data processing means an upper count level WU from the average value AV and standard deviation value SD as follows:

$$WU = AV + a \times SD$$

where a is a constant;

preparing a second conversion table representing a linear characteristic of conversion of count to photographic density such that the upper count level WU is displayed at said maximum photographic density on the film in said data processing means;

preparing, in said data processing means, by referring to said first and second conversion tables a third conversion table showing a characteristic of conversion of count to gray scale such that the upper count level WU is displayed the said maximum photographic density of the film;

converting detection data representing a scintigram of the subject into data signals having gray levels according to said third conversion table in said data processing means;

converting the data signals having gray levels into video signals according to a linear characteristic of conversion of gray scale to amplitude level in said data processing means; and photographing the scintigram image of the subject on the film by supplying the video signals to said imaging means.

* * * * *

UNITED STATES PATENT AND TRADEMARK OFFICE
CERTIFICATE OF CORRECTION

PATENT NO. : 4,864,500
DATED : September 05, 1989
INVENTOR(S) : Takashi Ichihara It is certified that error appears in the above-identified patent and that said Letters Patent is hereby corrected as shown below:

<u>In the Claims</u>

Claim 2, Column 7, Line 54, change "x-ray" to --X-ray--.

Claim 3, Column 7, Line 67, change "reach" to --read--.

Signed and Sealed this

Twenty-third Day of June, 1992

Attest:

DOUGLAS B. COMER

*Attesting Officer*   *Acting Commissioner of Patents and Trademarks*